US012630550B2

(12) United States Patent
Janda et al.

(10) Patent No.: US 12,630,550 B2
(45) Date of Patent: May 19, 2026

(54) PHARMACOPHORE FOR TRAIL INDUCTION

(71) Applicant: THE SCRIPPS RESEARCH INSTITUTE, La Jolla, CA (US)

(72) Inventors: Kim D. Janda, La Jolla, CA (US); Nicholas T. Jacob, San Diego, CA (US); Jonathan W. Lockner, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 8 days.

(21) Appl. No.: 18/391,420

(22) Filed: Dec. 20, 2023

(65) Prior Publication Data

US 2024/0190877 A1 Jun. 13, 2024

Related U.S. Application Data

(63) Continuation of application No. 17/372,894, filed on Jul. 12, 2021, now Pat. No. 11,891,392, which is a continuation of application No. 16/848,032, filed on Apr. 14, 2020, now abandoned, which is a continuation of application No. 16/359,633, filed on Mar. 20, 2019, now Pat. No. 10,633,385, which is a continuation of application No. 15/126,192, filed as application No. PCT/US2015/023362 on Mar. 30, 2015, now Pat. No. 10,239,877.

(60) Provisional application No. 61/972,689, filed on Mar. 31, 2014.

(51) Int. Cl.
*C07D 471/14* (2006.01)
*A61K 31/519* (2006.01)

(52) U.S. Cl.
CPC .......... *C07D 471/14* (2013.01); *A61K 31/519* (2013.01)

(58) Field of Classification Search
CPC ............................ C07D 471/14; A61K 31/519
See application file for complete search history.

(56) References Cited

U.S. PATENT DOCUMENTS

| | | | |
|---|---|---|---|
| 10,239,877 B2 | 3/2019 | Janda | |
| 2014/0271540 A1* | 9/2014 | Stogniew | ................ A61P 35/00 424/85.4 |
| 2014/0335048 A1 | 11/2014 | Stogniew | |
| 2016/0264574 A1 | 9/2016 | Stogniew | |
| 2017/0107221 A1 | 4/2017 | Janda | |

FOREIGN PATENT DOCUMENTS

| | | |
|---|---|---|
| CN | 102970868 | 3/2013 |
| CN | 106456643 | 2/2017 |
| DE | 2150062 | 4/1973 |
| JP | 2011522893 A | 8/2011 |
| JP | 2013525308 | 6/2013 |
| JP | 6132833 | 4/2017 |
| JP | 2017511321 | 4/2017 |
| WO | 2011130628 | 10/2011 |
| WO | 2012138789 | 10/2012 |
| WO | 2015073072 A1 | 5/2015 |
| WO | 2015153468 | 10/2015 |

OTHER PUBLICATIONS

Office Action from corresponding Canadian Application No. 2944452, dated Apr. 26, 2021.
U.S. Appl. No. 15/126,192, Response filed Sep. 21, 2017 to Non-Final Office Action mailed Jun. 22, 2017, 7 pgs.
European Application Serial No. 15772254.7, Response to Extended European Search Report mailed Jul. 18, 2017, 10 Pgs.
U.S. Appl. No. 15/126,192, Non Final Office Action mailed Jun. 22, 2017, 9 pgs.
U.S. Appl. No. 15/126,192, Response filed Jan. 25, 2018 to Non Final Office Action mailed Oct. 2, 2017, 7 pgs.
Japanese Application Serial No. 2016-559887, Notice of Reasons for Rejection mailed Dec. 3, 2018, (w English Irranslation), 10 pages.
U.S. Appl. No. 15/126,192, Restriction Requirement mailed Apr. 12, 2017, 8 pgs.
International Application Serial No. PCT US2015 023362, Written Opinion mailed Jul. 8, 2015, 4 pgs.
Chemscene. TIC10, [Online]. Retrieved from the Internet: URL:http: www.chemscene.com TIC10.html, (2012), 2 pgs.
Chemical Book. ONC201,TIC10., [Online]. Retrieved from the Internet: URL:http: www.chemicalbook.com ChemicalProductProperty_EN_CB12711459.htm, (2010), 1 pg.
Calvert Research and Oncoceutics Announce Investment Partnership to Advance ONC201 to an IND Filing, Calvert Labs, [Online]. Retrieved from the Internet: URL:http: calvert-research.com 2013 10 calvert-research-and-Oncoceutics-announce-investment-partnership-to-advance-onc201-to-an-ind-filing , (Oct. 1, 2013), 2 pgs.
International Application Serial No. PCT US2015 023362, International Search Report mailed Jul. 8, 2015, 4 pgs.
U.S. Appl. No. 14/857,418, Statement and Affidavit for Reissue Application of U.S. Pat. No. 8,673,923, 1led Sep. 17, 2015, 65 pgs.
Chinese Application Serial No. 201580021658.3, Office Action mailed Aug. 3, 2018, (w English Translation), (Aug. 3, 2018), B pages.
U.S. Appl. No. 15/126,192, Ex Parte Quayle Action mailed May 25, 2018, 4 pgs.
U.S. Appl. No. 15/126,192, Notice of Allowance mailed Oct. 30, 2018, 7 pgs.
International Application Serial No. PCT US2015 023362, International Preliminary Report on Patentability mailed Oct. 13, 2016, 6 pgs.

(Continued)

*Primary Examiner* — Erich A Leeser
(74) *Attorney, Agent, or Firm* — Barnes & Thornburg LLP; Amy H. Fix; Aisha R. Hasan

(57) ABSTRACT

There are disclosed imidazolinopyrimidinone compounds that have activity to induce TRAIL gene expression in macrophages. There is further disclosed a method for treating various cancers comprising administering effective amounts of an imidazolinopyrimidinone having the structure of Formula I herein.

13 Claims, 7 Drawing Sheets

Specification includes a Sequence Listing.

(56) References Cited

OTHER PUBLICATIONS

U.S. Appl. No. 15/126,192, Response filed Apr. 24, 2017 to Restriction Requirement mailed Apr. 12, 2017, 5 pgs.
U.S. Appl. No. 15/126,192, Response filed Oct. 19, 2018 to Ex Parte Quayle Office Action mailed May 25, 2018, 5pgs.
European Application Serial No. 15772254.7, Communication Pursuant to Article 94(3) EPC mailed Apr. 3, 2018, 4 pgs.
U.S. Appl. No. 15/126,192, Non Final Office Action mailed Oct. 2, 2017, 6 pgs.
U.S. Appl. No. 15/126,192, Examiner Interview Summary mailed Sep. 13, 2018, 3 pgs.
European Application Serial No. 15772254.7, Extended European Search Report mailed Jul. 18, 2017, 9 pgs.
Japanese Application Serial No. 2016-559887, Examiners Decision of Final Refusal mailed May 15, 2019, w English translation, 4 pgs.
Chinese Application Serial No. 201580021658.3, Response filed Feb. 18, 2019 to Office Action mailed Aug. 3, 2018, with English claims, 17 pgs.
Japanese Application Serial No. 2016-559867, Response filed Mar. 22, 2019 to Notice of Reasons for Rejection mailed Dec. 3, 2018, with English claims, 23 pgs.
Allen, J.E., "Dual Inactivation of Akt and ERK by TIC10 Signals Foxo3a Nuclear Translocation, Trail Gene Induction, and Potent Antitumor Effects", Science Translational Medicine, vol. 5, No. 171, (Feb. 6, 2013), 15 pgs.
Ishizawa, "ONC201 Exerts p53-Independent Cytotoxicity Through Trail and DR5 Induction in Mantle Cell Lymphomas", [Online). Retrieved from the Internet: URL: http: www.bloodjoumal.org content 122 21 3822?sso-checked=true, (Nov. 15, 2013), 3 pgs.
Nicholas, T Jacob, Pharmacophore Reassignment for Induction of the Immunosurvei1 lance Cytokine Trail, Angewandte Chemie International Edition vol. 53, No. 26XP055259380 ISSN: 1433-7851, 001:10.1002 I: lanie.201402133, (Jun. 23, 2014), 6628-6631 pgs.
Reiter et al., "On Triazoles XVIII. An unexpected rearrangement observed during the reaction of 5-amino-1,2,4-triazoles with N-heterocyclic β-oxo-esters", Journal of Heterocyclic Chemistry, vol. 26, No. 4, (1989), Abstract only.
Wagner et al., "The angular structure of ONC201, a Trail pathway-inducing compound, determines its potent anti-cancer activity", Oncotarget, vol. 5, No. 24, Jan. 2015.

* cited by examiner

Linear (inactive)

1

Angular (active)

2

9

Linear
(inactive)

1

Angular
(active)

2

PHARMACOPHORE FOR TRAIL INDUCTION

CROSS-REFERENCE TO RELATED APPLICATIONS

This application is a continuation of U.S. application Ser. No. 17/372,894, filed Jul. 12, 2021, which is a continuation of U.S. application Ser. No. 16/848,032, filed Apr. 14, 2020, which is a continuation of U.S. patent application Ser. No. 16/359,633, filed on Mar. 20, 2019, now U.S. Pat. No. 10,633,385, which is a continuation of U.S. patent application Ser. No. 15/126,192, filed on Sep. 14, 2016, now U.S. Pat. No. 10,239,877, which is a U.S. national stage application filed under 35 U.S.C. § 371 from International Application Serial No. PCT/US2015/023362, which filed on Mar. 30, 2015, and published as WO 2015/153468 on Oct. 8, 2015, which claims the benefit of priority to U.S. Provisional Application Ser. No. 61/972,689, filed Mar. 31, 2014, which applications and publication are incorporated by reference as if reproduced herein and made a part hereof in their entirety, and the benefit of priority of each of which is claimed herein.

STATEMENT REGARDING SEQUENCE LISTING

The Sequence Listing associated with this application is provided in XML format in lieu of paper copy, and is hereby incorporated by reference into the specification. The name of the XML file containing the Sequence Listing is "89719-403928 Sequence Listing." The XML file is 5.74 KB, and was created on Feb. 7, 2024, and is being submitted electronically via Patent Center.

STATEMENT OF GOVERNMENT SUPPORT

The present invention was made with government support under HHSN27200700038C, AI077644, AI079436, and AI094348, awarded by the National Institutes of Health. The U.S. government has certain rights in the invention.

BACKGROUND

Cancer immunosurveillance relies on various effector functions of the immune system that can modify both induced and spontaneous carcinogenesis. TRAIL is an immunosurveillence cytokine critically involved in this process due to its ability to selectively induce apoptosis in cancer cells over normal cells (S. R. Wiley, K. Schooley, P. J. Smolak, W. S. Din, C. P. Huang, J. K. Nicholl, G. R. Sutherland, T. D. Smith, C. Rauch, C. A. Smith, *Immunity* 1995, 3, 673-682; A. Ashkenazi, V. M. Dixit, *Science* 1998; H. Walczak, R. E. Miller, K. Ariail, B. Gliniak, T. S. Griffith, M. Kubin, W. Chin, J. Jones, A. Woodward, T. Le, et al., *Nat. Med.* 1999, 5, 157-163; and A. Ashkenazi, R. C. Pai, S. Fong, S. Leung, D. A. Lawrence, S. A. Marsters, C. Blackie, L. Chang, A. E. McMurtrey, A. Hebert, et al., *J. Clin. Invest.* 1999, 104, 155-162). The TRAIL gene is expressed in a variety of tissues and cells (S. R. Wiley, K. Schooley, P. J. Smolak, W. S. Din, C. P. Huang, J. K. Nicholl, G. R. Sutherland, T. D. Smith, C. Rauch, C. A. Smith, *Immunity* 1995, 3, 673-682); including dendritic cells, natural killer (NK) cells, and monocytes/macrophages (M. J. Smyth, K. Takeda, Y. Hayakawa, J. J. Peschon, M. R. M. van den Brink, H. Yagita, *Immunity* 2003, 18, 1-6.). Its gene expression is under control of several transcriptional regulators, such as transcription factors NF-κB and p53 (K. Kuribayashi, G. Krigsfeld, W. Wang, J. Xu, P. A. Mayes, D. T. Dicker, G. S. Wu, W. S. El-Deiry, *Cancer Biol. Ther.* 2008, 7, 2034-2038.). Reduction of TRAIL expression by neutralizing antibodies and ablation of TRAIL expression in mice lacking the TRAIL gene results in the development of carcinogen-induced fibrosarcomas, sarcomas, and lymphomas; especially in p53-deficient mice (E. Cretney, K. Takeda, H. Yagita, M. Glaccum, J. J. Peschon, M. J. Smyth, *J. Immunol.* 2002; and K. Takeda, M. J. Smyth, E. Cretney, Y. Hayakawa, N. Kayagaki, H. Yagita, K. Okumura, *J. Exp. Med.* 2002, 195, 161-169). These data are also consistent with observations that change in TRAIL expression in immune cells is associated with TRAIL resistance in cancer cells (N. S. M. Azahri, M. M. Kavurma, *Cell. Mol. Life Sci.* 2013, 70, 3617-3629). Thus, effectors of TRAIL production in immune cells are of clinical relevance (M. J. Smyth, K. Takeda, Y. Hayakawa, J. J. Peschon, M. R. M. van den Brink, H. Yagita, *Immunity* 2003, 18, 1-6.) and could also be used as a means to achieve a model system for studying the complex immunosurveillance signaling system

SUMMARY

The invention is directed, in various embodiments, to a compound and pharmaceutical composition comprising an effective amount of a compound capable of inducing expression of TRAIL gene in cells capable of expressing the TRAIL gene to produce the cytokine TRAIL. TRAIL (a cytokine) can selectively induce apoptosis in cancer cells over normal cells. Therefore, the present disclosure provides a compound and pharmaceutical that is effective for treating various cancers. Without being bound by theory, the disclosed compound and pharmaceutical composition induces expression of TRAIL.

In various embodiments, the invention is directed to a compound of formula (I)

(I)

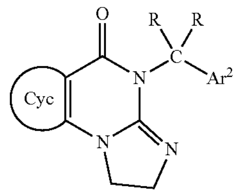

wherein

- Cyc is a single 5- to 8-membered heterocyclyl ring comprising at least one nitrogen atom, with a group of formula $Ar^1$—$CR_2$-being bonded to the nitrogen atom;
- $Ar^1$ and $Ar^2$ are each independently selected aryl groups which are independently substituted with 0, 1, or 2 J groups;
- each independently selected R is H or is (C1-C6)alkyl;
- J is (C1-C6)alkyl, (C3-C9)cycloalkyl, (C3-C9)cycloalkyl (C1-C6)alkyl, or halo;
- or a pharmaceutically acceptable salt thereof.

The present disclosure provides a pharmaceutical composition comprising a compound selected from the group consisting of

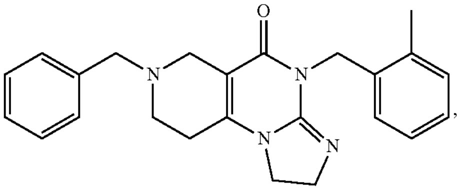

,

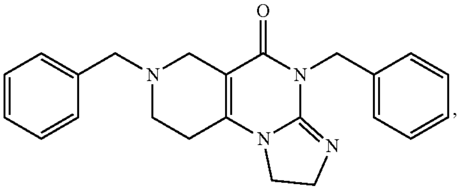

,

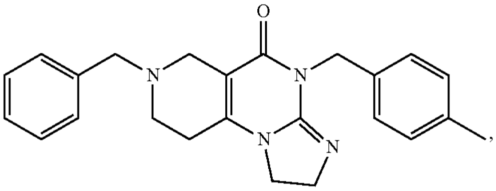

,

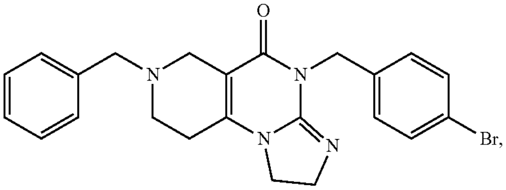

,

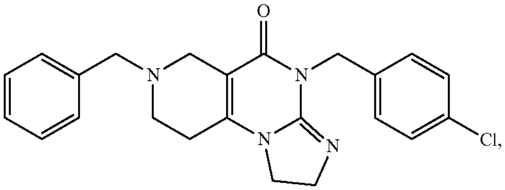

,

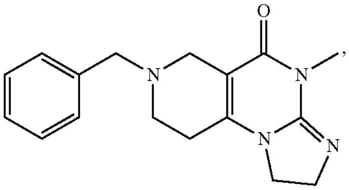

, and

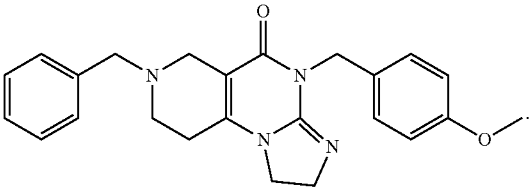

.

In various embodiments, the compound used to induce TRAIL is compound 2

(2)

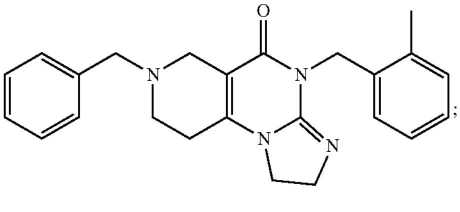

;

or a pharmaceutically acceptable salt thereof. The IUPAC name for compound 2 is 7-benzyl-4-(2-methylbenzyl)-1,2,6,7,8,9-hexahydroimidazo[1,2-a]pyrido[3,4-e]pyrimidin-5(4H)-one.

The present disclosure provides a method for treating various cancers, comprising administering to a patient an effective amount of a compound of formula (I), such as compound 2. The method for treating a broad spectrum of mammalian cancers, wherein the broad spectrum of mammalian cancers to be treated is selected from the group consisting of ovarian, colon, breast, liver, pancreas, gastro-intestinal, head-and neck, cervix, prostate, lung cancers, melanomas, glioblastomas, myelomas, neuroblastic-derived CNS tumors, monocytic leukemias, B-cell derived leukemias, T-cell derived leukemias, B-cell derived lymphomas, T-cell derived lymphomas, and mast cell derived tumors, and combinations thereof.

DETAILED DESCRIPTION

Figure 1:
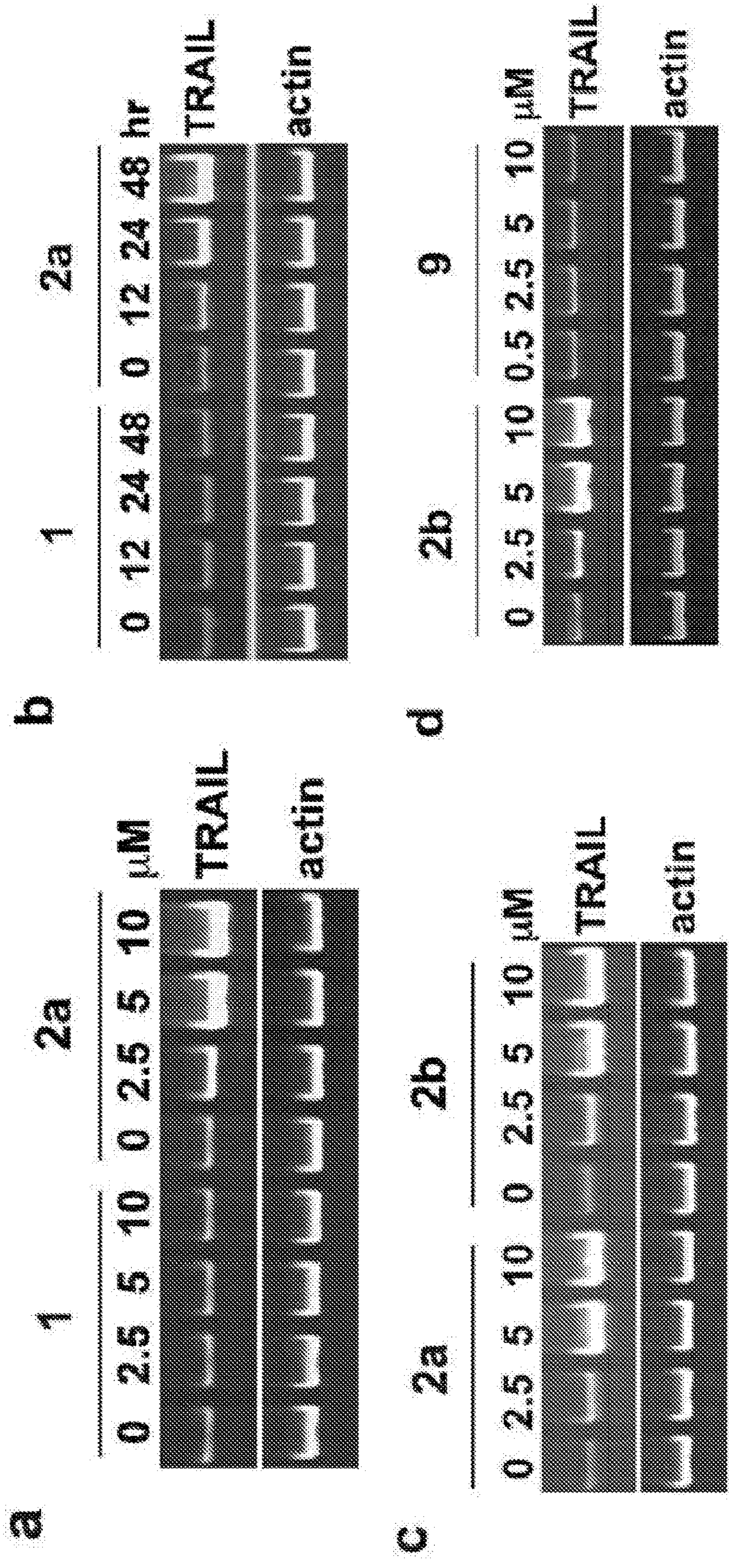
FIG. 1 shows a) Induction of TRAIL mRNA in RAW cells treated for 48 h with indicated dose of linear isomer (1) or angular isomer 2; b) Induction of TRAIL mRNA induction to 5 μM compound 1 and compound 2 for indicated times. c) Dose-dependent response to compound 2a and compound 2b. d) Dose-dependent response to angular (2) and compound 9. Compound 2a is a sample obtained from the NCI repository, compound 2b is a compound synthesized herein; both were shown to be a compound of structure 2.
Figure 2:
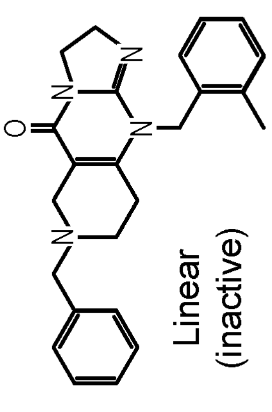
FIG. 2 shows a comparison of the imidazolinopyrimidanone structures of inactive compound 1 and active compound 2 with respect to TRAIL expression. The structures of each were confirmed by X-ray crystallographic analysis.
Figure 2:
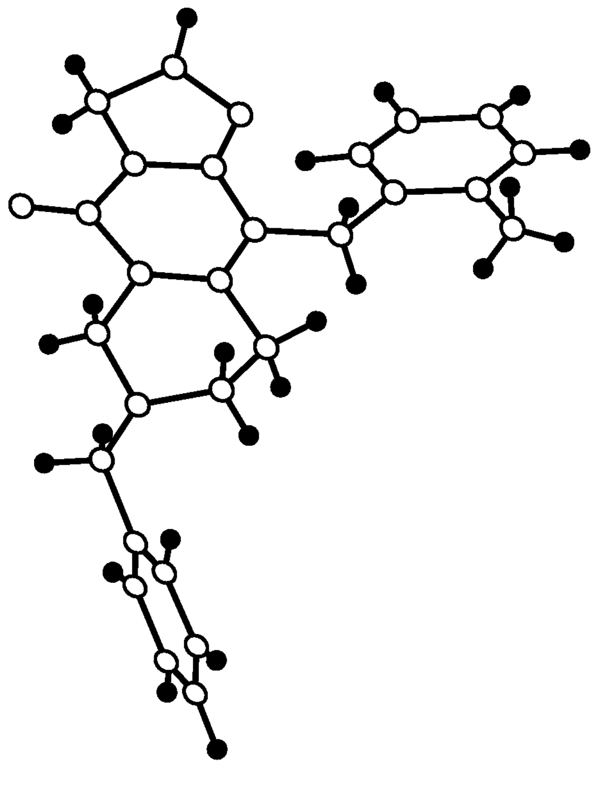
Figure 2:
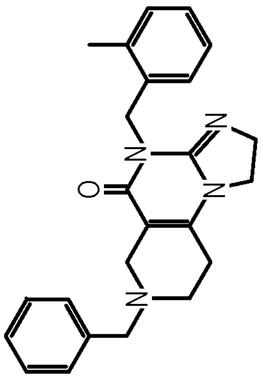
Figure 2:
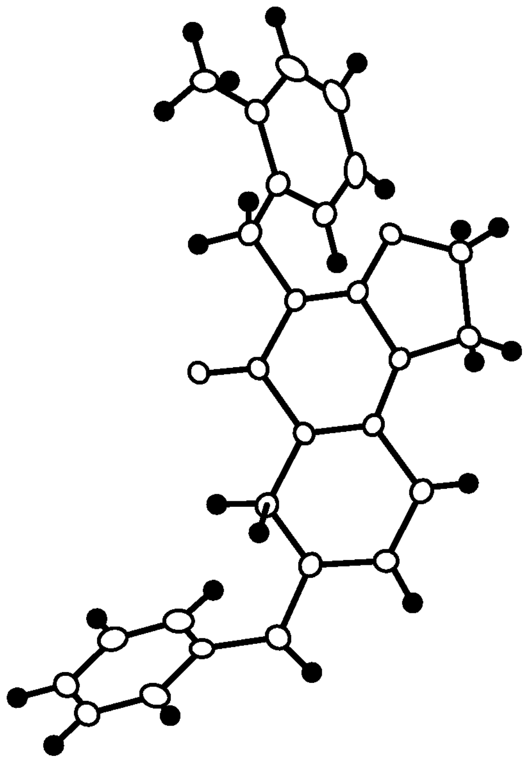
Figure 3:
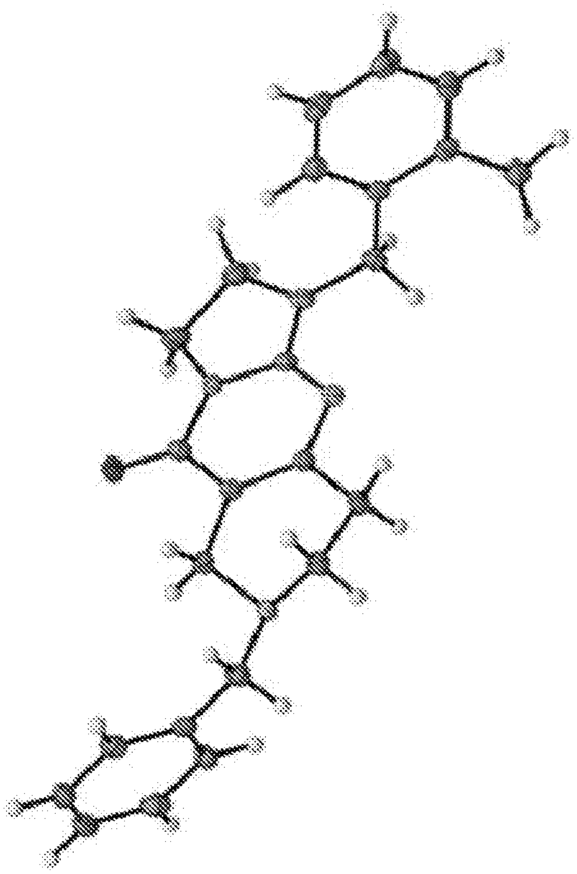
FIG. 3 shows the structure of constitutional isomer, compound 9.
Figure 3:
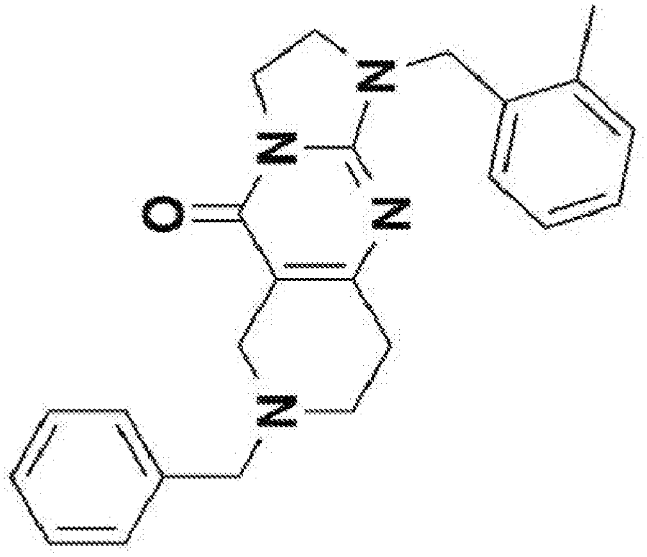
Figure 4:
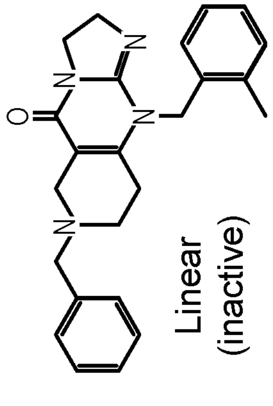
FIG. 4 shows comparative structures of compound 1 and compound 2.
Figure 4:
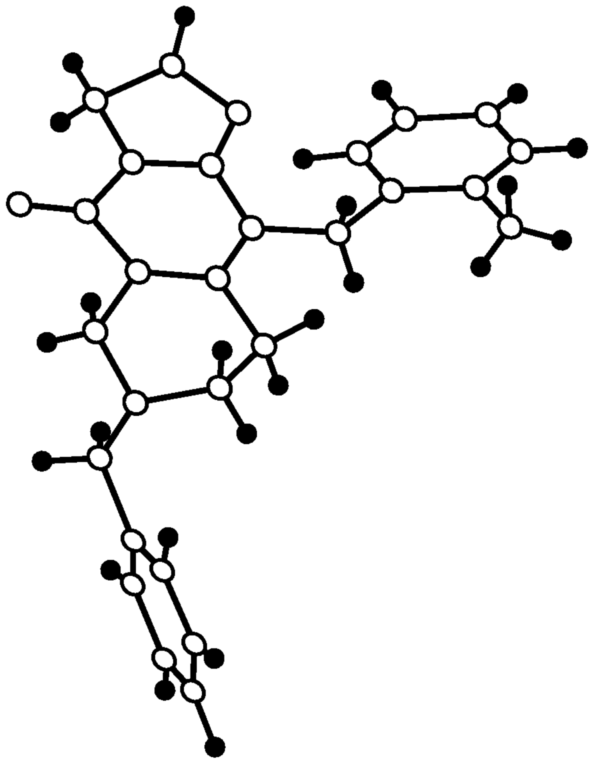
Figure 4:
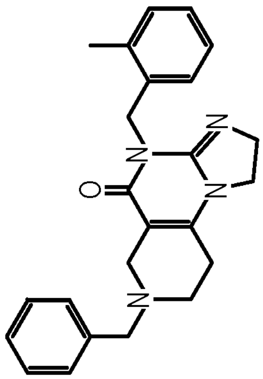
Figure 4:
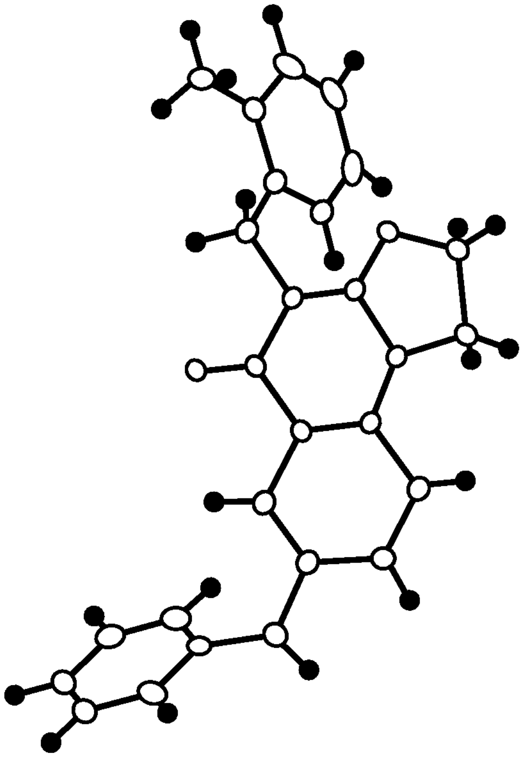

The present disclosure provides a compound of formula (I)

(I)

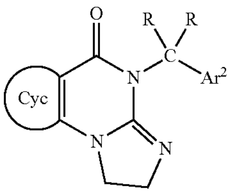

wherein

Cyc is a 5- to 8-membered monocyclic heterocyclyl ring comprising one nitrogen atom, with a group of formula $Ar^1$—$CR_2$-being bonded to the ring nitrogen atom;

$Ar^1$ and $Ar^2$ are each independently aryl groups which are substituted with 0, 1, or 2 J groups;

R is independently H or (C1-C6)alkyl;

J is independently (C1-C6)alkyl, (C3-C9)cycloalkyl, (C3-C9)cycloalkyl(C1-C6)alkyl, halo, or (C1-C6)haloalkyl;

or a pharmaceutically acceptable salt thereof.

Preferably, the compound of formula (I) is a compound within the subgenus formula (IA)

(IA)

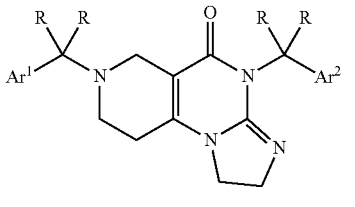

or a pharmaceutically acceptable salt thereof.

More specifically, the compound of formula (IA) is a compound wherein $Ar^1$ and $Ar^2$ are each a phenyl group substituted with 0, 1, or 2 J groups; and, R at each occurrence is independently H or (C1-C6)alkyl;

or a pharmaceutically acceptable salt thereof.

Preferably, the compound of formula (I) is compound 2

(2)

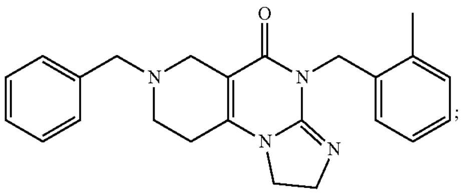

or a pharmaceutically acceptable salt thereof.

In various embodiments, the invention provides a compound of formula (I) that is not compound 2.

The present disclosure further provides a method for treating various cancers, comprising administering an effective amount of a compound of formula (I)

(I)

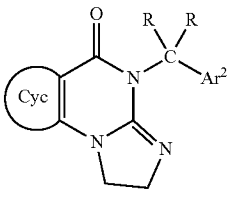

wherein

Cyc is a 5- to 8-membered monocyclic heterocyclyl ring comprising one nitrogen atom, with a group of formula $Ar^1$—$CR_2$-being bonded to the nitrogen atom;

$Ar^1$ and $Ar^2$ are aryl groups which are substituted with 0, 1, or 2 J groups;

R is independently H or (C1-C6)alkyl;

J is independently (C1-C6)alkyl, (C3-C9)cycloalkyl, (C3-C9)cycloalkyl(C1-C6)alkyl, halo, or (C1-C6)haloalkyl;

or a pharmaceutically acceptable salt thereof.

Preferably, the compound is a compound selected from the subgenus of formula (IA)

(IA)

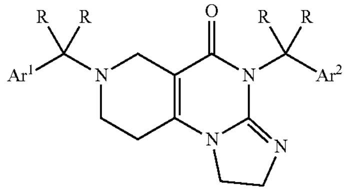

or a pharmaceutically acceptable salt thereof.

More preferably, in the compound of formula (IA), $Ar^1$ and $Ar^2$ is a phenyl group substituted with 0, 1, or 2 J groups.

Most preferably the compound of formula (I) is compound 2

(2)

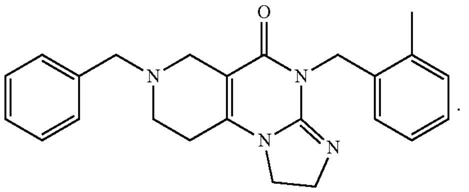

In various embodiments, the invention provides a method for treating various cancers with a compound of formula (I) wherein the compound of formula (I) is not compound 2.

The method can be used for treating a broad spectrum of mammalian cancers, wherein the broad spectrum of mammalian cancers to be treated is selected from the group consisting of ovarian, colon, breast, liver, pancreas, gastrointestinal, head-and neck, cervix, prostate, lung cancers, melanomas, glioblastomas, myelomas, neuroblastic-derived CNS tumors, monocytic leukemias, B-cell derived leukemias, T-cell derived leukemias, B-cell derived lymphomas, T-cell derived lymphomas, and mast cell derived tumors, and combinations thereof.

Another imidazolinopyrimidinone, (called compound 1 herein) in disclosed in United States patent application 20120276088 published 1 Nov. 2012. This patent application discloses linear compound 1 which is used for comparison purposes herein. We synthesized compound 1 in four steps from 4-chloronicotinic acid (Scheme 1).

Scheme 1

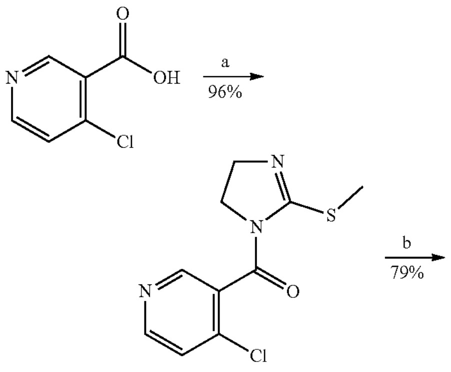

3

-continued

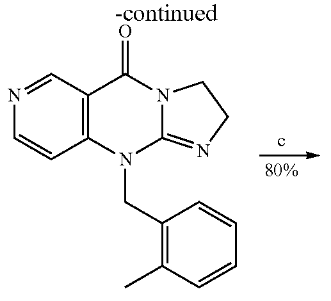

4

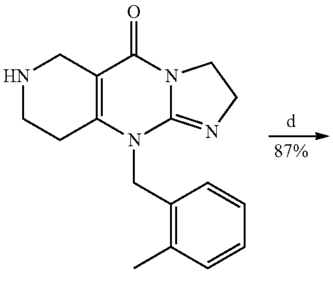

5

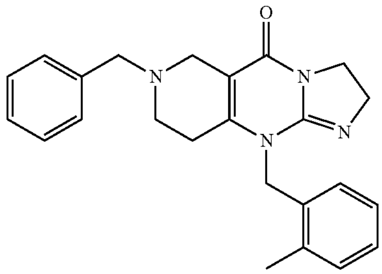

1

Synthesis of compound 1: (a) $SOCl_2$, 90° C., 1 h, then 2-methylthioimidazoline hydroiodide, $Et_3N$, $CH_2Cl_2$, 0° C. to rt, 19 h, 96%; (b) 2-methylbenzylamine, $K_3PO_4$, N,N-dimethylacetamide, reflux, 1 h, 79%; (c) 45 psi $H_2$(g), $PtO_2$, MeOH/TFA, rt, 5 h, 80%; (d) benzaldehyde, $Na(OAc)_3BH$, AcOH, $CH_2Cl_2$, rt, 4 h, 87%.

Briefly, acylation of an activated carboxylic acid, followed by a double displacement reaction, and subsequent hydrogenation and reductive amination afforded compound 1 in 52% overall yield. This structure of compound 1 was confirmed by mass spectrometry, nuclear magnetic resonance (NMR) spectroscopic, and X-ray crystallographic analyses (see Examples section).

The biological activity of compound 1 was measured by RT-PCR analysis of TRAIL mRNA expression in the murine macrophage cell line RAW 264.7. No change in TRAIL mRNA expression over controls was observed, even at doses as high as 10 μM (FIG. 1*a*) or with prolonged exposure (FIG. 1*b*). As shown in FIG. 1, compound 2a, (obtained from the NCl), exhibits the desired TRAIL bioactivity, as did synthesized compound 2b, but synthesized compound 1 does not. Therefore, there is a need in the art to create a biologically active imidazolinopyrimidinone, which is the more angular compound of formula (I), and in particular compound 2.

Compound 2 was prepared in three steps in 82% yield (Scheme 2). A synthetic product, termed herein compound 2b, was obtained, and its structure confirmed as 2.

Scheme 2

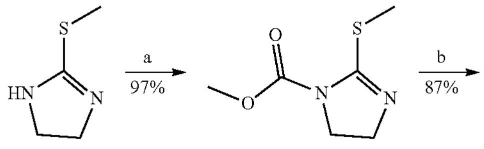

6

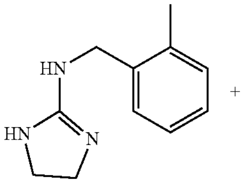

7

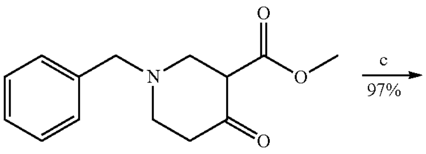

8

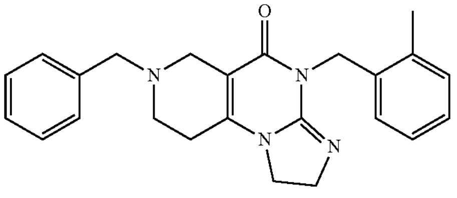

2

Synthesis of compound 2: (a) methyl chloroformate, $Et_3N$, $CH_2Cl_2$, 0° C. to rt, 44 h, 97%; (b) 2-methylbenzylamine, MeOH, AcOH, reflux, 45 h, 87%; (c) NaOMe, MeOH, reflux, 18 h, 97%.

A mixture of guanidine 7 and 1-benzyl-4-oxopiperidine-3-carboxylate hydrochloride (8) in refluxing methanol and sodium methoxide afforded 2b almost exclusively; a trace amount of 1 was detected by $^1H$ NMR following work-up of this reaction, but was removed by subsequent purification. We rationalize this result by considering that the imidazolinyl nitrogens of 7 possess both statistical and steric advantages over the benzylic nitrogen of 7. Initial attack by nitrogen at the ketone carbonyl of 8 affords an aminocarbinol intermediate, which suffers intramolecular cyclocondensation to provide synthetic sample 2b. Its structure 2 was confirmed by mass spectrometry and NMR spectroscopy.

Compound 2, obtained as synthetic sample 2b was able to induce TRAIL mRNA expression, as did repository compound 2a (FIG. 1*c*).

Therefore, angular compound 2 (shown by the inventors herein to be the active TRAIL induction factor) has the structure (2)

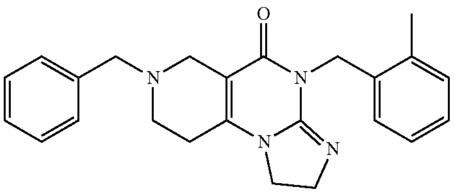

Compound 1 (does not seem to be active) has the structure (1)

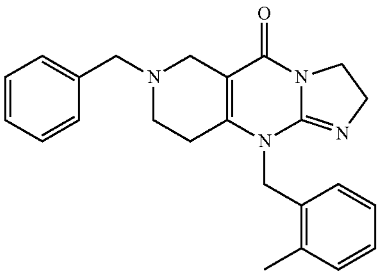

;

and the isomeric linear compound to have the structure 9

(9)

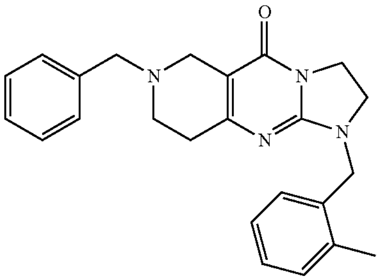

.

Of these three compounds, only compound 2 exhibits the desired TRAIL bioactivity.

X-ray crystal structures, taken as described in the Examples section, are provided in the Figures.

These findings provide a structure-activity relationship wherein the angular fusion of the tricyclic core is a necessity of the pharmacophore for TRAIL induction in macrophages.

Our three-step synthesis of compound 2 began with the preparation of carbamate 6 (T. Smejkal, D. Gribkov, J. Geier, M. Keller, B. Breit, *Chemistry* 2010, 16, 2470-2478) and its conversion to guanidine 7 (W. K. Fang, P. X. Nguyen, K. Chow, T. M. Heidelbaugh, D. G. Gomez, M. E. Garst, S. C. Sinha, Allergan Inc., USA, 2011). If the 1,1-diamine is unsymmetrical, an isomeric mixture of products is possible (see: J. V. Greenhill, M. J. Ismail, P. N. Edwards, P. J. Taylor, J Chem Soc Perk T 2 1985, 1255-1264; C. Romano, E. Delacuesta, C. Avendano, F. Florencio, J. Sainzaparicio, Tetrahedron 1988, 44, 7185-7192; F. Esser, K. H. Pook, A. Carpy, Synthesis-Stuttgart 1990, 72-78). A mixture of guanidine 7 and 1-benzyl-4-oxopiperidine-3-carboxylate hydrochloride in refluxing methanol (with the aid of NaOMe) afforded compound 2 almost exclusively; a trace amount of compound 1 was detected by $^1$H NMR following work-up of this reaction. We rationalize this result by considering that the imidazolinyl nitrogens of 7 possess both statistical and steric advantages over the benzylic nitrogen of 7. Initial attack by nitrogen at the ketone carbonyl affords an aminocarbinol intermediate, which suffers intramolecular cyclocondensation to provide 2.

The $K_2CO_3$-mediated reaction of a β-keto ester with a 2-amino-2-oxazoline (a type of unsymmetrical 1,1-diamine) affords a mixture of linear and angular products (I. Forfar, C. Jarry, M. Laguerre, J. M. Leger, I. Pianet, *Tetrahedron* 1999, 55, 12819-12828). The authors accumulated empirical and theoretical evidence to support the notion that "the endocyclic nitrogen atom is the most nucleophilic and attacks the most electrophilic carbon of the biselectrophile. A ring closure between the exocyclic nitrogen atom and the second electrophilic center concludes the bicyclic heterocycle synthesis." This is consistent with our own observations in the synthesis of 7 via a similar strategy.

To reiterate the salient feature of the present synthesis, by using sodium methoxide in refluxing methanol (M. F. Koehler, P. Bergeron, E. Blackwood, K. K. Bowman, Y. H. Chen, G. Deshmukh, X. Ding, J. Epler, K. Lau, L. Lee, L. Liu, C. Ly, S. Malek, J. Nonomiya, J. Oeh, D. F. Ortwine, D. Sampath, S. Sideris, L. Trinh, T. Truong, J. Wu, Z. Pei, J. P. Lyssikatos, *J. Med. Chem.* 2012, 55, 10958-10971), compound 2 is produced nearly exclusively. If the condensation is performed in the presence of base and/or at higher temperature, then sufficient means are available for statistically and sterically more likely aminocarbinol intermediate to suffer rapid intramolecular cyclocondensation leading to compound 2.

In addition, releated compounds A through R were synthesized. The characteristics of compounds A through R are provided in Table 1 below:

TABLE 1

| Compound Label | Structure | Chemical Info |
|---|---|---|
| A | 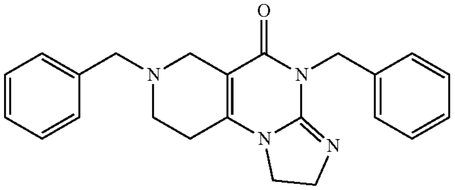 [SMILES: O=C1C2=C(CCN(Cc3ccccc3)C2)N2CCN=C2N1Cc1ccccc1] | Chemical Formula: C23H24N4O<br>Molecular Weight: 372.47<br>Log P: 2.6 |
| B | 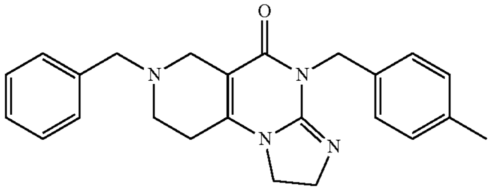 [SMILES: Cc1ccc(CN2C(=O)C3=C(CCN(Cc4ccccc4)C3)N3CCN=C23)cc1] | Chemical Formula: C24H26N4O<br>Molecular Weight: 386.50<br>Log P: 3.09 |

TABLE 1-continued

| Compound Label | Structure | Chemical Info |
|---|---|---|
| C | 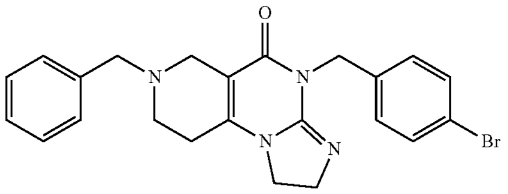 [SMILES: O=C1C2=C(CCN(Cc3ccccc3)C2)N2CCN=C2N1Cc1ccc(Br)cc1] | Chemical Formula: C23H23BrN4O<br>Molecular Weight: 451.37<br>Log P: 3.43 |
| D | 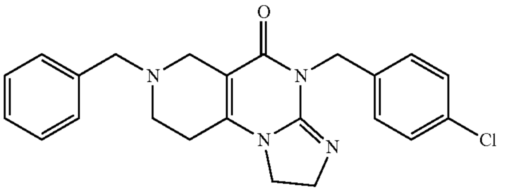 [SMILES: O=C1C2=C(CCN(Cc3ccccc3)C2)N2CCN=C2N1Cc1ccc(Cl)cc1] | Chemical Formula: C23H23ClN4O<br>Molecular Weight: 406.91<br>Log P: 3.16 |
| E | 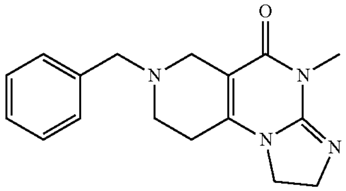 [SMILES: CN1C(=O)C2=C(CCN(Cc3ccccc3)C2)N2CCN=C12] | Chemical Formula: C17H20N4O<br>Molecular Weight: 296.37<br>Log P: 0.87 |
| F | 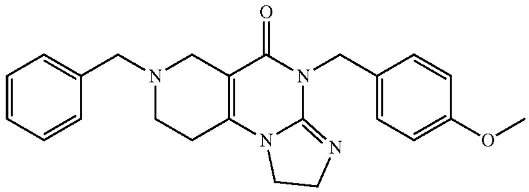 [SMILES: COc1ccc(CN2C(=O)C3=C(CCN(Cc4ccccc4)C3)N3CCN=C23)cc1] | Chemical Formula: C24H26N4O2<br>Molecular Weight: 402.50<br>Log P: 2.47 |
| G | 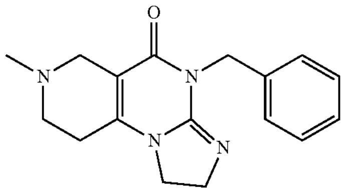 [SMILES: CN1CCC2=C(C1)C(=O)N(Cc1ccccc1)C1=NCCN12] | Chemical Formula: C17H20N4O<br>Molecular Weight: 296.37<br>Log P: 0.87 |
| H | 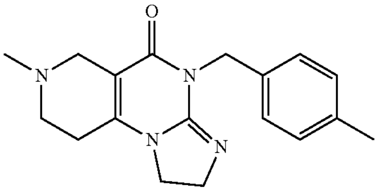 | Chemical Formula: C18H22N4O<br>Molecular Weight: 310.40<br>Log P: 1.35 |
| I | 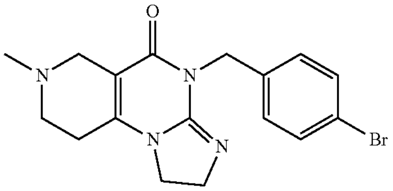 [SMILES: CN1CCC2=C(C1)C(=O)N(Cc1ccc(Br)cc1)C1=NCCN12] | Chemical Formula: C17H19BrN4O<br>Molecular Weight: 375.27<br>Log F: 1.7 |
| J | 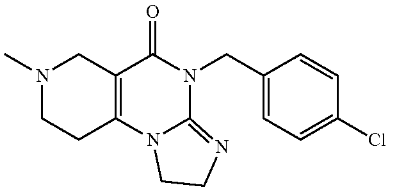 [SMILES: CN1CCC2=C(C1)C(=O)N(Cc1ccc(Cl)cc1)C1=NCCN12] | Chemical Formula: C17H19ClN4O<br>Molecular Weight: 330.82<br>Log P: 1.42 |

TABLE 1-continued

| Compound Label | Structure | Chemical Info |
|---|---|---|
| K | 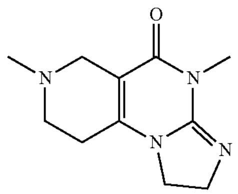 | Chemical Formula: C11H16N4O<br>Molecular Weight: 220.28<br>Log P: −0.87 |
| L | 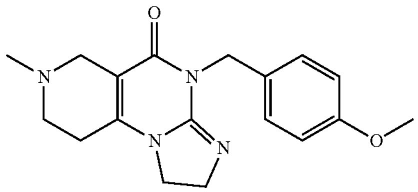 | Chemical Formula: C18H22N4O2<br>Molecular Weight: 326.40<br>Log P: 0.74 |
| M | 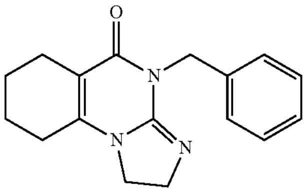 [SMILES: O=C1C2=C(CCCC2)N2CCN=C2N1Cc1ccccc1] | Chemical Formula: C17H19N3O<br>Molecular Weight: 281.36<br>Log P: 2.29 |
| N | 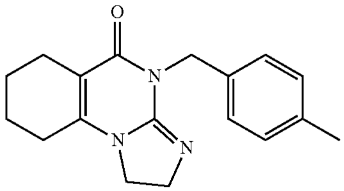 [SMILES: Cc1ccc(CN2C(=O)C3=C(CCCC3)N3CCN=C23)cc1] | Chemical Formula: C18H21N3O<br>Molecular Weight: 295.39<br>Log P: 2.78 |
| O | 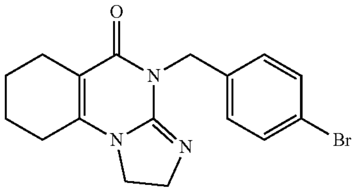 [SMILES: O=C1C2=C(CCCC2)N2CCN=C2N1Cc1ccc(Br)cc1] | Chemical Formula: C17H18BrN3O<br>Molecular Weight: 360.26<br>Log P: 3.12 |
| P | 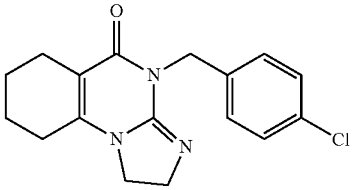 [SMILES: O=C1C2=C(CCCC2)N2CCN=C2N1Cc1ccc(Cl)cc1] | Chemical Formula: C17H18ClN3O<br>Molecular Weight: 315.80<br>Log P: 2.85 |
| Q | 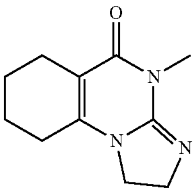 | Chemical Formula: C11H15N3O<br>Molecular Weight: 205.26<br>Log P: 0.56 |

TABLE 1-continued

| Compound Label | Structure | Chemical Info |
| --- | --- | --- |
| R | 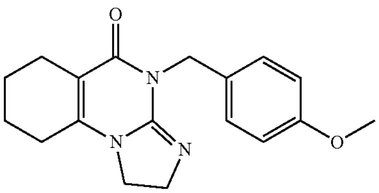 | Chemical Formula: C18H21N3O2<br>Molecular Weight: 311.38<br>Log P: 2.17 |

As used herein, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

The term "disease" or "disorder" or "malcondition" are used interchangeably, and are used to refer to diseases or conditions wherein TRAIL, such as inducing expression of the TRAIL gene in a cell, plays a role in the biochemical mechanisms involved in the disease or malcondition or symptom(s) thereof such that a therapeutically beneficial effect can be achieved with an effective amount or concentration of a synthetic ligand of the invention adequate to induce expression of TRAIL and induce apoptosis, e.g., selectively in cancer cells. For example, the cancers to be treated by the compounds of the present disclosure include a broad spectrum of mammalian cancers, wherein the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, and mast cell derived tumors, and combinations thereof.

The expression "effective amount", when used to describe therapy to an individual suffering from a disorder, refers to the quantity or concentration of a compound of the invention that is effective to induce expression of TRAIL in the individual's tissues.

The terms "halo" or "halogen" or "halide" by themselves or as part of another substituent mean, unless otherwise stated, a fluorine, chlorine, bromine, or iodine atom, preferably, fluorine, chlorine, or bromine.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

EXAMPLES

General Procedures

All reactions were carried out under an argon atmosphere with dry solvents using anhydrous conditions unless otherwise stated. Chemicals were purchased from Acros Organics, Oakwood Products, and Sigma-Aldrich. They were used as received unless otherwise noted. Dry dichloromethane ($CH_2Cl_2$) was obtained via distillation over calcium hydride ($CaH_2$). Dry methanol (MeOH) was obtained via distillation over magnesium turnings. Reagents were purchased at the highest commercial quality and used without further purification, unless otherwise stated. Yields refer to chromatographically and spectroscopically ($^1H$ NMR) homogeneous materials, unless otherwise stated. Reactions were monitored by thin layer chromatography (TLC) carried out on 0.25 mm E. Merck silica gel plates (60F-254) using UV light as the visualizing agent, or basic aqueous potassium permanganate ($KMnO_4$), and heat as developing agent. E. Merck silica gel (60, particle size 0.040-0.063 mm) was used for flash column chromatography. Preparative thin layer chromatography (PTLC) separations were carried out on 0.50 mm E. Merck silica gel plates (60F-254). Concentration of organic solvents was performed on a rotary evaporator under reduced pressure followed by further evacuation using a dual stage mechanical pump. NMR spectra were recorded on Bruker DRX-600, DRX-500, and AMX-400 instruments and calibrated using residual undeuterated solvent as an internal reference ($CHCl_3$@δ 7.26 ppm $^1H$ NMR, δ 77.16 ppm $^{13}C$ NMR; $CD_3OD$@δ 4.87 ppm $^1H$ NMR, δ 49.00 ppm $^{13}C$ NMR). The following abbreviations (or combinations thereof) were used to explain $^1H$ NMR multiplicities: s=singlet, d=doublet, t=triplet, m=multiplet, br=broad. High-resolution mass spectra (HRMS) were recorded on Agilent LC/MSD TOF mass spectrometer by electrospray ionization time-of-flight reflectron experiments. IR spectra were recorded on either a PerkinElmer Spectrum 100 FTIR spectrometer with ATR accessory or a Jasco 480 Plus FTIR spectrometer. Melting points were recorded on a Fisher-Johns 12-144 melting point apparatus and are uncorrected.

Synthetic Procedures

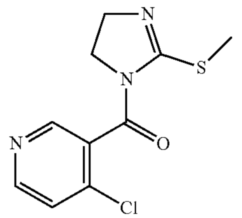 [SMILES: CSC1=NCCN1C(=O)c1cnccc1Cl]

(4-Chloropyridin-3-yl)(2-(methylthio)-4,5-dihydro-1H-imidazol-1-yl)methanone (3)

A mixture of 4-chloronicotinic acid (1.00 g, 6.35 mmol) and $SOCl_2$ (15 mL) was stirred at 90° C.for 1 h. Removal of $SOCl_2$ by rotary evaporation gave 4-chloronicotinic acid chloride hydrochloride as a pale yellow solid, which was placed under argon balloon, cooled to 0° C., and dissolved in $CH_2Cl_2$ (45 mL). A solution of 2-methylthio-2-imidazoline hydriodide (1.32 g, 5.40 mmol) and $Et_3N$ (2.92 mL, 20.95 mmol) in $CH_2Cl_2$ (75 mL) was added via cannula. The pale amber solution was stirred at room temperature overnight. After 19 h, $CH_2Cl_2$ (150 mL) was added and the resulting solution washed with saturated aqueous $NaHCO_3$ (2×100 mL) and brine (2×100 mL). The organic layer was dried ($Na_2SO_4$) and concentrated in vacuo. Purification by silica gel chromatography (19:1 $CH_2Cl_2$/MeOH) afforded 3 (1.32 g, 96%) as a pale yellow syrup.

$R_f$=0.19 (silica gel, 19:1 $CH_2Cl_2$/MeOH)

IR (neat) $\nu_{max}$ 1661, 1574, 1377, 1200, 903, 724 $cm^{-1}$ $^1H$ NMR (600 MHZ, $CDCl_3$) δ 8.56 (d, J=5.5 Hz, 1 H), 8.54 (s, 1 H), 7.37 (d, J=5.2 Hz, 1 H), 4.15-3.65 (m, 2 H), 3.93 (t, J=8.3 Hz, 2 H), 2.37 (s, 3 H)

$^{13}C$ NMR (150 MHz, $CDCl_3$) δ 162.1, 151.9, 148.6, 131.9, 124.7, 54.1, 48.5, 15.6 HRMS (ESI-TOF) calcd. for $C_{10}H_{10}ClN_3OSH^+$ [M+H$^+$] 256.0306, found 256.0309

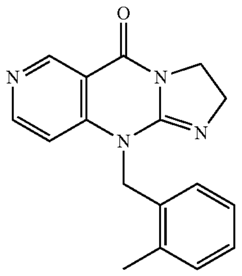 [SMILES: Cc1ccccc1CN1C2=NCCN2C(=O)c2cnccc21]

10-(2-Methylbenzyl)-2,3-dihydroimidazo[1,2-a]pyrido[4,3-d]pyrimidin-5(10H)-one (4)

A mixture of 3 (1.30 g, 5.08 mmol), 2-methylbenzylamine (1.89 mL, 15.25 mmol), powdered $K_3PO_4$ (1.08 g, 5.08 mmol), and N,N-dimethylacetamide (10 mL) was heated at reflux for 1 h. The resulting mixture was cooled and partitioned between $CH_2Cl_2$ (30 mL) and $H_2O$ (30 mL). The organic layer was dried ($Na_2SO_4$) and concentrated in vacuo. Purification by silica gel chromatography (19:1 $CH_2Cl_2$/MeOH) and trituration with cold hexanes afforded 4 (1.17 g, 79%) as a white solid.

m.p. 182-188° C. (hexanes)

$R_f$=0.32 (silica gel, 19:1 $CH_2Cl_2$/MeOH)

IR (neat) $\nu_{max}$ 1674, 1634, 1591, 1455, 1400, 1284, 747 $cm^{-1}$ $^1H$ NMR (500 MHZ, $CDCl_3$) δ 9.15 (s, 1 H), 8.45 (d, J=5.9 Hz, 1 H), 7.23 (d, J=7.4 Hz, 1 H), 7.19 (t, J=7.4 Hz, 1 H), 7.11 (t, J=7.4 Hz, 1 H), 6.84 (d, J=7.7 Hz, 1 H), 6.55 (d, J=5.9 Hz, 1 H), 5.21 (s, 2 H), 4.20 (t, J=8.9 Hz, 2 H), 3.96 (t, J=8.9 Hz, 2 H), 2.41 (s, 3 H)

$^{13}C$ NMR (150 MHz, $CDCl_3$) δ 158.0, 154.6, 151.0, 150.2, 147.7, 135.0, 131.6, 131.0, 127.8, 126.7, 124.2, 111.9, 107.9, 50.2, 46.7, 45.3, 19.2

HRMS (ESI-TOF) calcd. for $C_{17}H_{16}N_4OH^+$ [M+H$^+$] 293.1397, found 293.1397

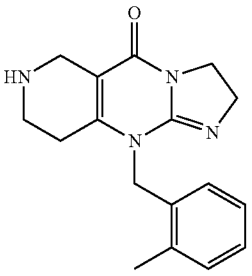 [SMILES: Cc1ccccc1CN1C2=NCCN2C(=O)C2=C1CCNC2]

10-(2-Methylbenzyl)-2,3,6,7,8,9-hexahydroimidazo[1,2-a]pyrido[4,3-d]pyrimidin-5(10H)-one (5)

A mixture of 4 (300 mg, 1.03 mmol), $PtO_2$ (60 mg), MeOH (3 mL), and TFA (3 mL) was hydrogenated (45 psi) in a Parr shaker for 5 h. The mixture was filtered through a Celite® pad to remove catalyst, then concentrated in vacuo. The colorless syrup was dissolved in 1:1 EtOAc/$H_2O$ (40 mL), made basic by addition of 2 M NaOH (10 mL), and layers were separated. The aqueous layer was extracted with EtOAc (40 mL). The combined organic layers were washed with brine (20 mL), dried ($Na_2SO_4$), and concentrated in vacuo. Purification by silica gel chromatography (19:1:0.1 $CH_2Cl_2$/MeOH/$NH_4$OH) afforded 5 (244 mg, 80%) as a white solid.

m.p. 170-174° C. (MeOH)

$R_f$=0.12 (silica gel, 19:1:0.1 $CH_2Cl_2$/MeOH/$NH_4$OH)

IR (neat) $\nu_{max}$ 3287, 1660, 1627, 1605, 1472, 1293, 919 $cm^{-1}$ $^1H$ NMR (600 MHZ, $CDCl_3$) δ 7.20-7.14 (m, 3 H), 6.92-6.90 (m, 1 H), 4.98 (s, 2 H), 4.05 (t, J=9.4 Hz, 2 H), 3.82 (t, J=9.4 Hz, 2 H), 3.68 (t, J=1.9 Hz, 2 H), 2.95 (t, J=5.8 Hz, 2 H), 2.30 (s, 3 H), 2.28-2.25 (m, 2 H), 1.66 (br s, 1 H)

$^{13}C$ NMR (150 MHz, $CDCl_3$) δ 160.0, 152.8, 147.2, 134.6, 133.8, 130.7, 127.4, 126.8, 123.7, 106.6, 49.9, 46.0, 45.2, 42.7, 42.2, 25.5, 19.1

HRMS (ESI-TOF) calcd. for $C_{17}H_{20}N_4OH^+$ [M+H$^+$] 297.1710, found 297.1709

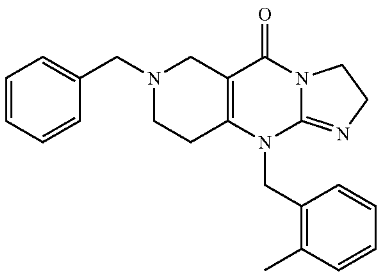 [SMILES: Cc1ccccc1CN1C2=NCCN2C(=O)C2=C1CCN(Cc1ccccc1)C2]

7-Benzyl-10-(2-methylbenzyl)-2,6,7,8,9,10-hexahydroimidazo[1,2-a]pyrido[4,3-d]pyrimidin-5(3H)-one (1)

A solution of 5 (230 mg, 0.78 mmol) and benzaldehyde (103 µL, 1.02 mmol) in $CH_2Cl_2$ (2.5 mL) was treated with AcOH (76 µL, 1.35 mmol) and $Na(OAc)_3BH$ (267 mg, 1.26 mmol) at room temperature. The mixture was stirred for 4 h, then diluted with $CH_2Cl_2$ (10 mL) and washed with saturated aqueous $NaHCO_3$ (10 mL). The aqueous layer was extracted with $CH_2Cl_2$ (10 mL). The combined organic layers were dried ($Na_2SO_4$) and concentrated in vacuo. Purification by silica gel chromatography (19:1 $CH_2Cl_2$/MeOH) afforded 1 (261 mg, 87%) as a white solid.

m.p. 166-168° C. (MeOH)

$R_f$=0.25 (silica gel, 19:1 $CH_2Cl_2$/MeOH)

IR (neat) $\nu_{max}$ 2866, 2358, 2339, 1616, 1456, 983 $cm^{-1}$ $^1H$ NMR (600 MHZ, $CDCl_3$) δ 7.37-7.28 (m, 4 H), 7.26-7.14 (m, 4 H), 6.93-6.91 (m, 1 H), 4.98 (s, 2 H), 4.06 (t, J=9.4 Hz, 2 H), 3.84 (t, J=9.4 Hz, 2 H), 3.64 (s, 2 H), 3.38 (s, 2 H), 2.54 (t, J=5.7 Hz, 2 H), 2.37 (t, J=5.5 Hz, 2 H), 2.29 (s, 3 H)

$^{13}C$ NMR (150 MHz, $CDCl_3$) δ 159.8, 152.9, 147.1, 137.6, 134.6, 133.7, 130.7, 129.2, 128.5, 127.5, 127.4, 126.8, 123.7, 105.7, 62.1, 49.9, 49.6, 48.6, 46.4, 45.3, 26.1, 19.1

HRMS (ESI-TOF) calcd. for $C_{24}H_{26}N_4OH^+$ [$M+H^+$] 387.2179, found 387.2189

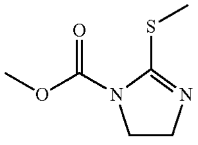

Methyl 2-(methylthio)-4,5-dihydro-1H-imidazole-1-carboxylate (6)

A solution of 2-methylthio-2-imidazoline hydriodide (12.21 g, 50 mmol) and $Et_3N$ (16 mL, 115 mmol) in $CH_2Cl_2$ (50 mL) at 0° C. was treated with methyl chloroformate (5.0 mL, 65 mmol) dropwise. The mixture was allowed to warm to room temperature and stirred overnight. After 44 h, the mixture was diluted with EtOAc (200 mL), stirred, then filtered to remove insoluble salts. The salts were rinsed with EtOAc (50 mL). The filtrate was concentrated in vacuo, affording 6 (8.47 g, 97%) as a white solid.

$R^f$=0.33 (silica gel, 19:1 $CH_2Cl_2$/MeOH)

IR (neat) $\nu_{max}$ 1717, 1576, 1429, 1378, 1218, 1023, 758 $cm^{-1}$ $^1H$ NMR (600 MHZ, $CDCl_3$) δ 3.92-3.85 (m, 4 H), 3.78 (s, 3 H), 2.41 (s, 3 H)

$^{13}C$ NMR (150 MHz, $CDCl_3$) δ 159.7, 152.5, 53.9, 53.2, 47.5, 15.2

HRMS (ESI-TOF) calcd. for $C_6H_{10}N_2O_2SH^+$ [$M+H^+$] 175.0536, found 175.0539

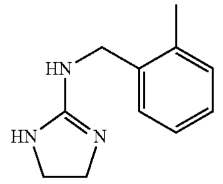

N-(2-Methylbenzyl)-4,5-dihydro-1H-imidazol-2-amine (7)

A solution of 6 (1.5 g, 8.61 mmol) and 2-methylbenzylamine (1.08 mL, 8.74 mmol) in MeOH (48 mL) was treated with AcOH (4.8 mL). The solution was stirred at a gentle reflux. After 45 h, the solution was cooled to room temperature and concentrated in vacuo. The residue was dissolved in $CH_2Cl_2$ (100 mL), washed with 1 M NaOH (55 mL), brine (55 mL), dried over $Na_2SO_4$, filtered, and concentrated in vacuo. Trituration with cold $CH_3CN$ afforded 7 (1.42 g, 87%) as a white solid.

$R_f$=0.14 (silica gel, 9:1:0.1 $CH_2Cl_2$/MeOH/$NH_4OH$)

IR (neat) $\nu_{max}$ 2862, 2358, 1684, 1635, 1521, 1349, 1238 $cm^{-1}$ $^1H$ NMR (600 MHZ, $CD_3OD$) δ 7.25-7.15 (m, 4 H), 4.34 (s, 2 H), 3.61 (s, 4 H), 2.32 (s, 3 H)

$^{13}C$ NMR (150 MHz, $CD_3OD$) δ 163.0, 161.5, 137.4, 136.7, 131.4, 128.8, 128.5, 127.2, 46.2, 45.8, 18.9

HRMS (ESI-TOF) calcd. for $C_{11}H_{15}N_3H^+$ [$M+H^+$] 190.1339, found 190.1344.

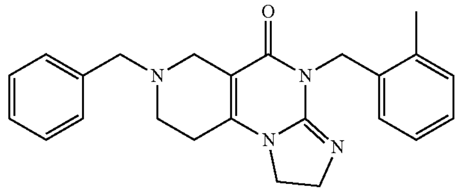

7-Benzyl-4-(2-methylbenzyl)-1,2,6,7,8,9-hexahydroimidazo[1,2-a]pyrido[3,4-e]pyrimidin-5(4H)-one (2)

A mixture of methyl 1-benzyl-4-oxopiperidine-3-carboxylate hydrochloride, 8, (568 mg, 2.0 mmol) and 7 (795 mg, 4.2 mmol) was treated with a solution of sodium methoxide in MeOH (0.5 M, 3.0 mL, 1.5 mmol). The mixture was stirred at a gentle reflux overnight. After 18 h, the reaction was cooled to room temperature, diluted with $CH_2Cl_2$ (50 mL), washed with brine (20 mL), dried over $Na_2SO_4$, filtered, and concentrated in vacuo. Purification by silica gel chromatography (19:1 $CH_2Cl_2$/MeOH) afforded 2 (753 mg, 97%) as a pale yellow solid.

m.p. 132-135° C. (MeOH)

$R_f$=0.25 (silica gel, 19:1 $CH_2Cl_2$/MeOH)

IR (neat) $\nu_{max}$ 2750, 2358, 1646, 1616, 1487, 1296, 738 $cm^{-1}$ $^1H$ NMR (500 MHZ, $CDCl_3$) δ 7.33 (m, 5 H), 7.11 (m, 4 H), 5.05 (s, 2 H), 3.89 (m, 4 H), 3.67 (s, 2 H), 3.32 (s, 2 H), 2.68 (m, 2 H), 2.51 (m, 2 H), 2.40 (s, 3 H)

$^{13}C$ NMR (150 MHz, $CDCl_3$) δ 161.6, 153.4, 145.8, 137.7, 135.7, 134.4, 130.4, 129.3, 128.6, 127.5, 127.0, 126.0, 125.4, 102.1, 62.5, 50.7, 49.7, 48.3, 47.1, 43.3, 27.0, 19.4

HRMS (ESI-TOF) calcd. for $C_{24}H_{26}N_4OH^+$ [$M+H^+$] 387.2179, found 387.2166

TABLE 1

| Comparison of 13C NMR chemical shifts for compounds 1, 2, and 9 | | | |
|---|---|---|---|
| JWL (1) | JWL (2) | NCI (2) | MK (9) |
| 159.8 | 161.6 | 161.5 | 160.7 |
| 152.9 | 153.4 | 153.4 | 160.4 |
| 147.1 | 145.8 | 145.8 | 154.5 |
| 137.6 | 137.7 | 137.6 | 138.4 |
| 134.6 | 135.7 | 135.7 | 137.0 |
| 133.7 | 134.4 | 134.3 | 133.6 |
| 130.7 | 130.4 | 130.3 | 130.9 |
| 129.2 | 129.3 | 129.3 | 129.3 |
| 128.5 | 128.6 | 128.6 | 129.0 |
| 127.5 | 127.5 | 127.5 | 128.5 |
| 127.4 | 127.0 | 126.9 | 128.2 |
| 126.8 | 126.0 | 126.0 | 127.3 |
| 123.7 | 125.4 | 125.3 | 126.3 |
| 105.7 | 102.1 | 102.2 | 109.2 |
| 62.1 | 62.5 | 62.4 | 62.7 |
| 49.9 | 50.7 | 50.5 | 50.1 |
| 49.6 | 49.7 | 49.6 | 49.6 |
| 48.6 | 48.3 | 48.3 | 46.9 |
| 46.4 | 47.1 | 47.1 | 44.5 |
| 45.3 | 43.3 | 43.3 | 40.6 |
| 26.1 | 27.0 | 26.9 | 32.4 |
| 19.1 | 19.4 | 19.4 | 19.3 |

Spectra were recorded at 150 MHz in $CDCl_3$.

X-Ray Crystal Structures

Figure 5:
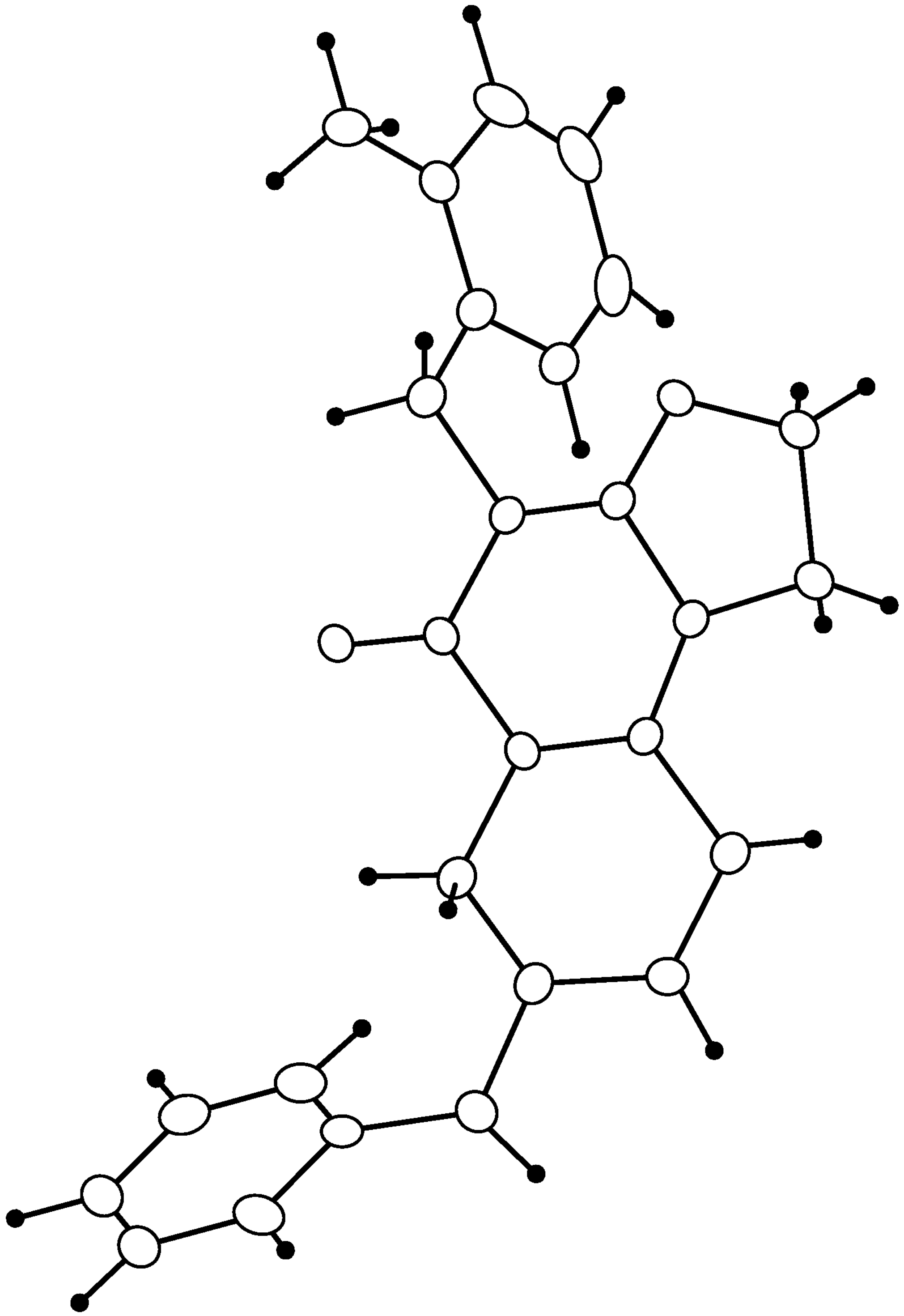
FIG. 5 shows the X-ray crystal structure obtained for compound 2.
Figure 6:
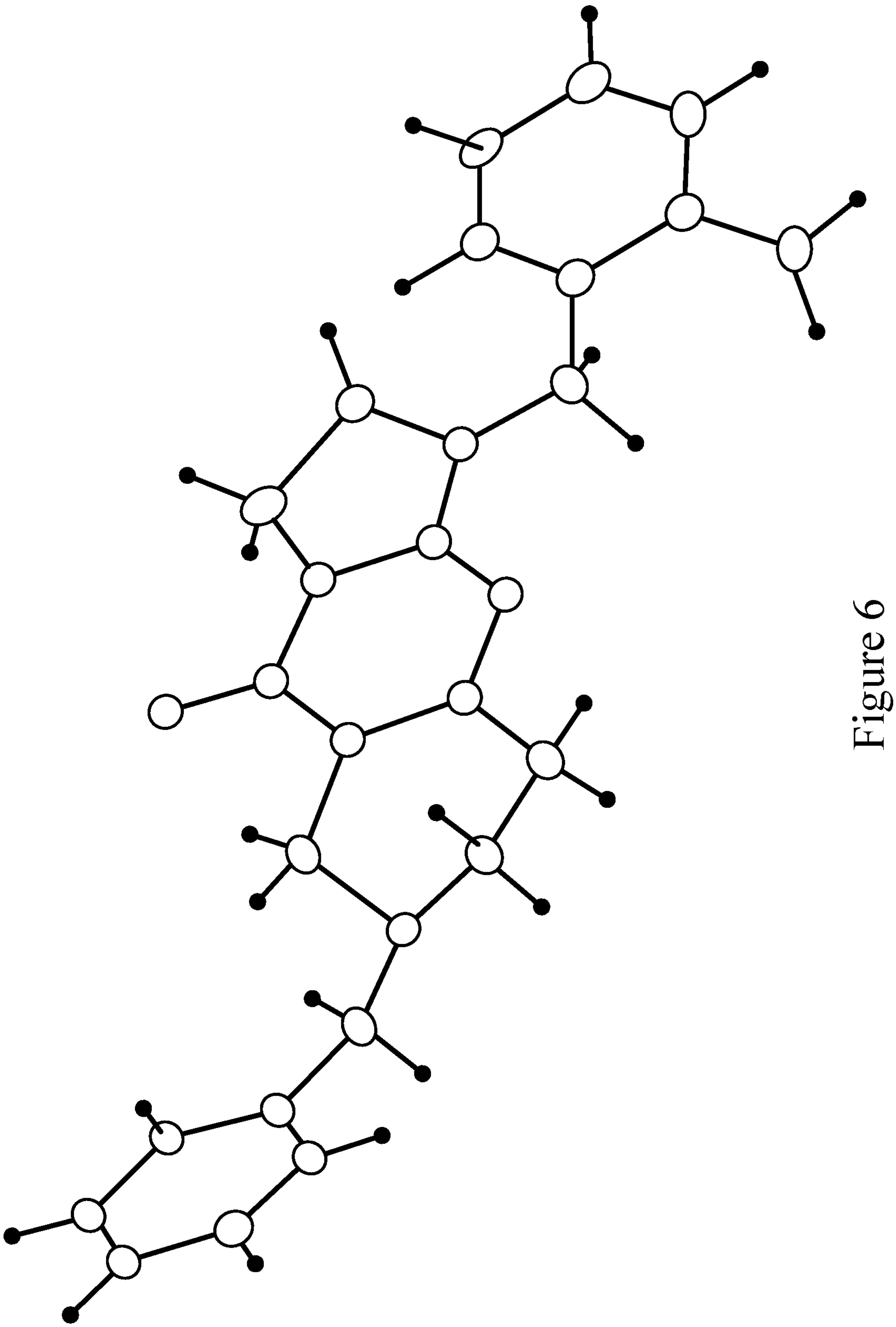
FIG. 6 shows the X-ray crystal structure obtained for compound 9.

The X-ray crystal structures of compounds 2 (as synthetic sample 2b) and 9 were obtained. The parameters are given below, and the structures obtained provided in FIGS. 5 and 6, respectively.

Compound 2 (Also Called HIPPO)

The single crystal X-ray diffraction studies were carried out on a Bruker X8 APEX II Ultra CCD diffractometer equipped with Mo Kα radiation (λ=0.71073). A 0.18×0.16×0.08 mm clear colorless plate of 2 was mounted on a Cryoloop with Paratone oil. Data were collected in a nitrogen gas stream at 100 K using $\overline{\omega}$ scans. Crystal-to-detector distance was 50 mm using 5 s exposure time with a 1.0° scan width. Data collection was 99.9% complete to 25.00° in θ. A total of 14019 reflections were collected covering the indices, −11<=h<=10, −11<=k<=11, −19<=l<=18. 4833 reflections were found to be symmetry independent, with a Rint of 0.0391. Indexing and unit cell refinement indicated a primitive, triclinic lattice. The space group was found to be P−1. The data were integrated using the Bruker SAINT software program and scaled using the SADABS software program. Solution by direct methods (SHELXT) produced a complete phasing model consistent with the proposed structure.

All non-hydrogen atoms were refined anisotropically by full-matrix least-squares (SHELXL). All hydrogen atoms were placed using a riding model. Their positions were constrained relative to their parent atom using the appropriate HFIX command in SHELXL.

Crystallographic data are summarized below. Full metrical parameters are available from the CCDC under number 981022. See FIG. 5.

-continued

| Crystal data and structure refinement for compound 2 | |
|---|---|
| Identification code | Janda01 (2) |
| Empirical formula | $C_{24}H_{26}N_4O$ |
| Molecular formula | $C_{24}H_{26}N_4O$ |
| Formula weight | 386.49 |
| Temperature | 100 K |
| Wavelength | 0.71073 Å |
| Crystal system | Triclinic |
| Space group | P-1 |
| Unit cell dimensions | a = 8.1173(11) Å α =85.638(3)° |
| | b = 8.4320(11) Å β = 85.045(3)° |
| | c = 14.6360(19) Å γ = 83.059(3)° |
| Volume | 988.5(2) $Å^3$ |
| Z | 2 |
| Density (calculated) | 1.298 $Mg/m^3$ |
| Absorption coefficient | 0.082 $mm^{-1}$ |
| F(000) | 412 |
| Crystal size | 0.18 × 0.16 × 0.08 $mm^3$ |
| Crystal color, habit | colorless plate |
| Theta range for data collection | 2.439 to 29.252° |
| Index ranges | −11 <= h <= 10, −11 <= k <= 11, −19 <= l <= 18 |
| Reflections collected | 14019 |
| Independent reflections | 4833 [R(int) = 0.0391] |
| Completeness to theta = 25.000° | 99.9% |
| Absorption correction | Semi-empirical from equivalents |
| Max. and min. transmission | 0.0976 and 0.0673 |
| Refinement method | Full-matrix least-squares on $F^2$ |
| Data/restraints/parameters | 4833/0/263 |
| Goodness-of-fit on $F^2$ | 1.027 |
| Final R indices [I > 2sigma(I)] | R1 = 0.0433, wR2 = 0.1082 |
| R indices (all data) | R1 = 0.0697, wR2 = 0.1181 |
| Extinction coefficient | n/a |
| Largest diff. peak and hole | 0.320 and −0.204 e.$Å^{-3}$ |

A colorless crystal of compound 9 was mounted on a Cryoloop with Paratone oil and data was collected at 100 K on a Bruker APEX II CCD with Mo $K_\alpha$ radiation (generated from a Mo rotating anode). Data was corrected for absorption with SADABS and structure was solved by direct methods.

All non-hydrogen atoms were refined anisotropically by full-matrix least-squares on $F^2$ and all hydrogen atoms were placed in calculated positions with appropriate riding parameters.

Highest peak 0.20 at 0.4224 0.6962 0.1821 [0.63 A from C9]

Deepest hole −0.23 at 0.0912 0.4660 0.3644 [0.93 A from C17]

Crystallographic parameters are summarized below. Full metrical parameters are available from the CCDC under number 981024. See FIG. 6.

| Crystal data and structure refinement for compound 9 | |
|---|---|
| Identification code | Janda03 (9) |
| Empirical formula | $C_{24}H_{26}N_4O$ |
| Molecular formula | $C_{24}H_{26}N_4O$ |
| Formula weight | 386.49 |
| Temperature | 100 K |
| Wavelength | 0.71073 Å |
| Crystal system | Triclinic |
| Space group | P-1 |
| Unit cell dimensions | a = 5.6439(18) Å a = 93.194(9)° |
| | b = 10.537(4) Å β = 91.021(6)° |
| | c = 16.502(5) Å γ = 96.745(5)° |
| Volume | 972.8(6) $Å^3$ |
| Z | 2 |
| Density (calculated) | 1.319 $Mg/m^3$ |
| Absorption coefficient | 0.083 $mm^{-1}$ |
| F(000) | 412 |
| Crystal size | 0.22 × 0.02 × 0.02 $mm^3$ |
| Crystal color, habit | colorless rod |
| Theta range for data collection | 1.95 to 26.34° |

-continued

| Crystal data and structure refinement for compound 9 | |
|---|---|
| Index ranges | $-6 <= h <= 6, -13 <= k <= 12, -20 <= l <= 18$ |
| Reflections collected | 10564 |
| Independent reflections | 3904 [R(int) = 0.0507] |
| Completeness to theta = 25.00° | 99.9% |
| Absorption correction | multi-scan/SADABS |
| Max. and min. transmission | 0.9983 and 0.9820 |
| Refinement method | Full-matrix least-squares on $F^2$ |
| Data/restraints/parameters | 3904/0/263 |
| Goodness-of-fit on $F^2$ | 1.003 |
| Final R indices [I > 2sigma(I)] | R1 = 0.0430, wR2 = 0.0942 |
| R indices (all data) | R1 = 0.0719, wR2 = 0.1068 |
| Largest diff. peak and hole | 0.201 and −0.229 e.$Å^{-3}$ |

BIOLOGICAL METHODS

Cell Culture Methods:

RAW 264.7 cells (ATCC TIB-71) were maintained in growth medium of Dulbecco's Modified Eagle's Medium (DMEM with 4.5 g/L glucose and pyruvate, Gibco BRL, Invitrogen Corp., USA) supplemented with L-glutamine, penicillin/streptomycin, non-essential amino acids (100× stocks, Invitrogen Corp.), 10 mM HEPES, pH 7.4 (1 M stock, Invitrogen), and 10% Fetal Bovine Serum (FBS, Hyclone); (V. V. Kravchenko, R. J. Ulevitch, G. F. Kaufmann, Methods Mol. Biol. 2011, 692, 133-145).

RNA RT-PCR Experiments:

Cells were plated in 6-well plates (Corning Costar 3506) diluted 1:5 in 3 mL growth medium, media was changed after cells had adhered. After 12 h incubation, cells were treated with described concentration of compound in DMSO, and incubated in the presence of that compound or vehicle for the described amount of time. At this time, media was removed and cells were treated with TRIzol reagent (Life Technologies), and RNA extracted via included protocol. RNA concentration determined using a Hitachi U-2000 UV-Vis Spectrophotometer and samples diluted to 12 μg/5 μL in H2O. This solution was diluted 1:5 in $H_2O$ and 1 μL of this solution was mixed with 50 μL of RT-PCR reaction mixture (Qiagen Onestep RT-PCR kit) and TRAIL primers.

Mouse: mTRAIL-F: 5'-GACACCATTTCTACAGTTCC-AG-3' (SEQ ID NO. 1), mTRAIL-R: 5'-CGGA-TAGCTGGTGTACTTGTAG-3' 3' (SEQ ID NO. 2).

Human: hTrail-F2: 5'-ACAGACCTGCGTGCTGATCG-TG-3' 3' (SEQ ID NO. 3) (exon 1) hTrail-R2: 5'-ACGAGCTGACGGAGTTGCCAC-3' 3' (SEQ ID NO. 4) (exon 2).

RT-PCR was run on an Applied Biosystems Gene Amp 9700 PCR system. RT-PCR products were analyzed on 5.5% acrylamide gel in TAE buffer (T. Maniatis, E. F. Fritsch, J. Sambrook, *Molecular Cloning: a Laboratory Manual*, Cold Spring Harbor Laboratory, Cold Spring Harbor, 1989).

Figure 7:
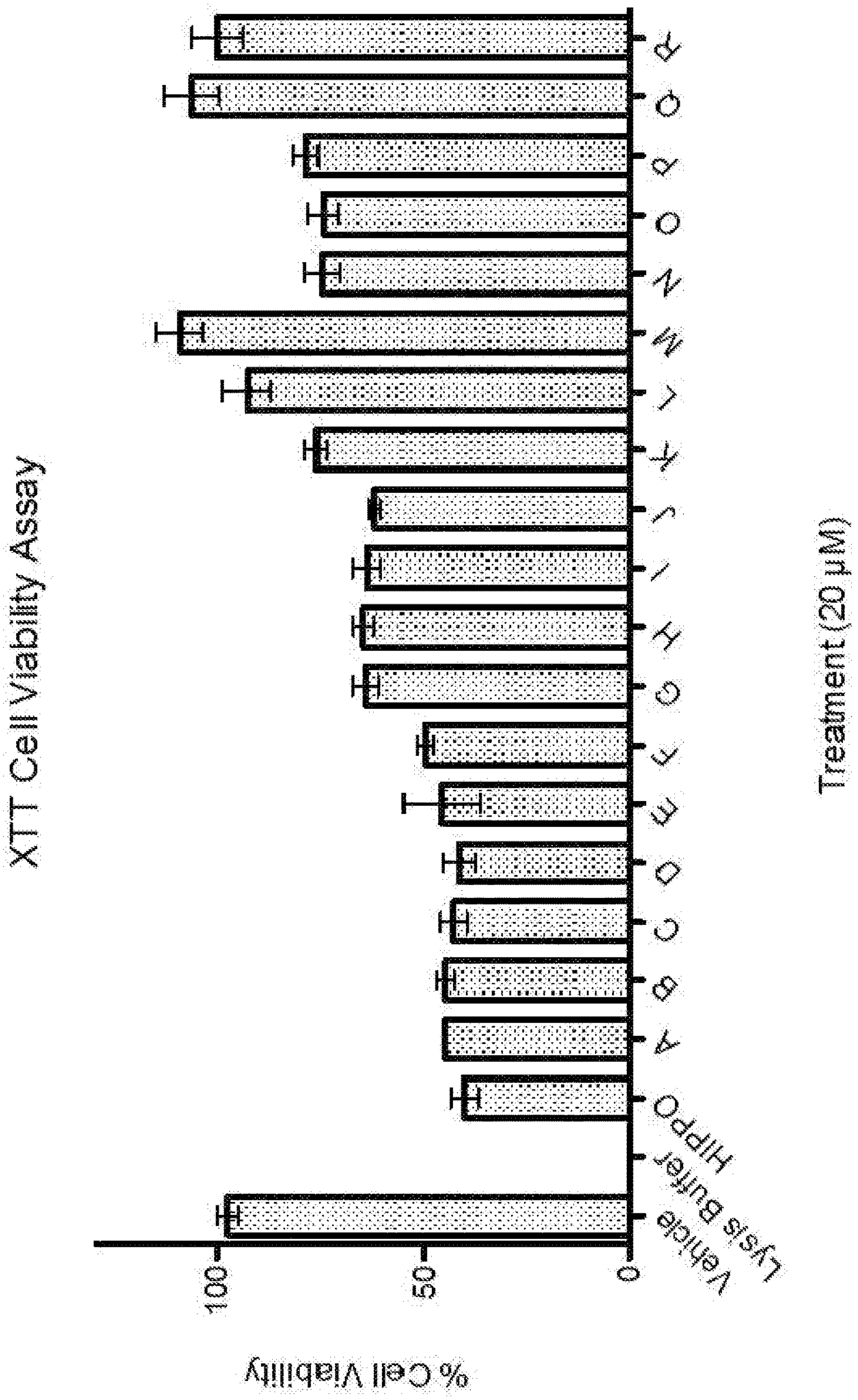
FIG. 7 shows a cell viability assay comparing the activity of a 20 mM concentration of various compounds including Compound 2 (HIPPO) and compounds A through R herein.

RAW 264.7 cells were plated at ~500 cell/well in Costar 96-well plates (Corning Inc, NY) in phenol-free Dulbecco's Modified Eagle's Medium (DMEM with 4.5 g/L glucose, Gibco BRL, Invitrogen Corporation, USA) supplemented with 10% fetal bovine serum (Gibco BRL, Invitrogen Corp., USA), L-glutamine, pyruvate, penicillin/streptomycin, and nonessential amino acids (100× stocks from Invitrogen). After 4 hours, cells were then treated in triplicate with vehicle, lysis buffer, 20 μM of compound 2 (HIPPO), or 20 μM of 18 derivative compounds (A through R) as listed in Table 1, above. After 48 hours, cell viability was assessed by colorimetric XTT formazan assay (Cell Signaling Tech.) according to manufacturer protocol. Relative absorbance was normalized to the vehicle treated cells (negative control) and lysis buffer treated cells (positive control) using Prism 5 for Mac (GraphPad). FIG. 7 summarizes the results of this assay. FIG. 7 shows a comparison of compounds A through R against HIPPO in their ability to attenuate proliferation of RAW 264.7 cancer cells. Compounds A through F exhibit similar activity to HIPPO, demonstrating that modification of the substituent of the amide nitrogen outside the tricyclic core is well tolerated and represents an auxophore.

What is claimed is:

1. A compound (2), (2)

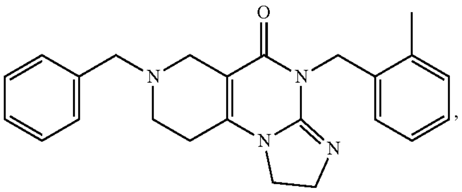

or a pharmaceutically acceptable salt thereof, substantially free of isomer compound (1), (1)

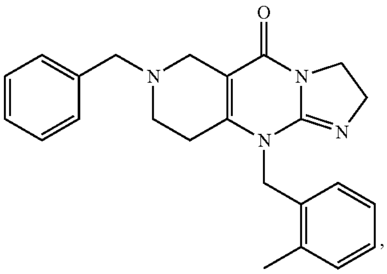

or a pharmaceutically acceptable salt thereof.

2. The compound according to claim 1, wherein the compound is further substantially free of isomer compound (9), (9)

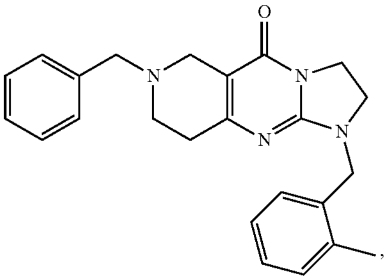

or a pharmaceutically acceptable salt thereof.

3. The compound according to claim 1, wherein presence of isomer compound (1) is determined by $^{1}$H NMR.

4. The compound according to claim 2, wherein presence of isomer compound (9) is determined by $^{1}$H NMR.

5. A compound (2), (2)

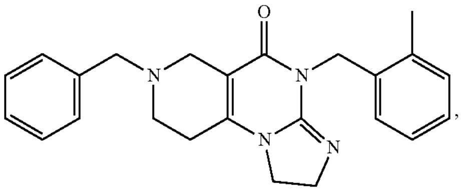

or a pharmaceutically acceptable salt thereof, obtained from a process comprising the step of contacting compound (7), (7)

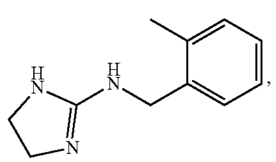

with compound (8), (8)

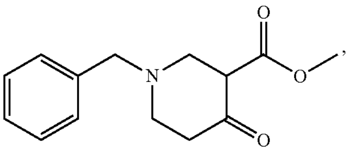

in refluxing methanol and sodium methoxide.

6. A composition comprising: a compound consisting essentially of isomer compound (2):

(2)

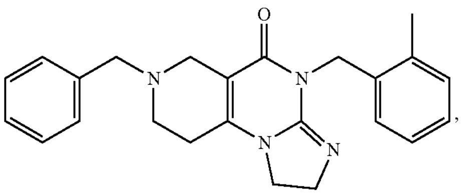

or a pharmaceutically acceptable salt thereof, and one or more pharmaceutically acceptable excipients.

7. A composition comprising the compound of claim 1, and one or more pharmaceutically acceptable excipients.

8. A composition comprising the compound of claim 2, and one or more pharmaceutically acceptable excipients.

9. A composition comprising the compound of claim 5, and one or more pharmaceutically acceptable excipients.

10. A composition comprising compound (2), (2)

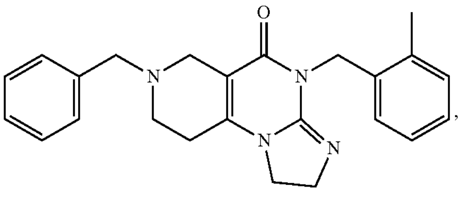

or a pharmaceutically acceptable salt thereof, wherein compound (2) is obtained from a process comprising the step of contacting compound (7), (7)

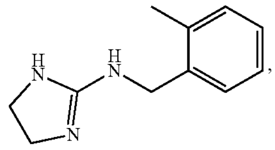

with compound (8)

(8)

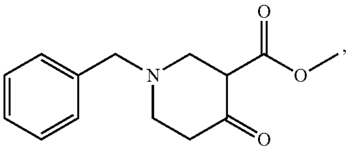

in refluxing methanol and sodium methoxide; and the composition further comprises one or more pharmaceutically acceptable excipient.

11. A composition comprising:

a) a compound that induces expression of TNF-related apoptosis-inducing ligand (TRAIL); and b) one or more pharmaceutically acceptable excipients, wherein the compound (a) consists essentially of isomer compound (2), (2)

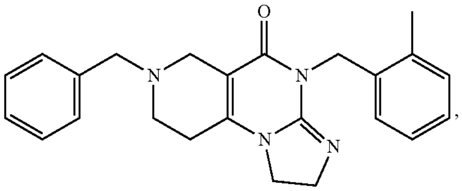

or a pharmaceutically acceptable salt thereof.

12. The composition according to claim 11, wherein the compound (a) is free of isomer compound (1), (1)

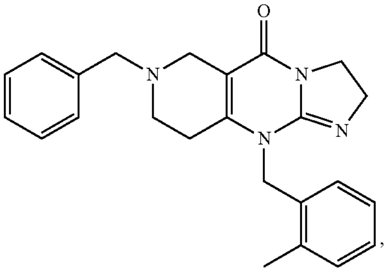

or a pharmaceutically acceptable salt thereof.

13. The composition according to claim 11, wherein the compound (a) is free of compound (9), (9)

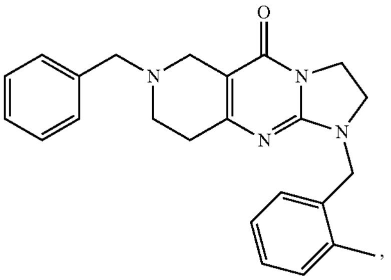

or a pharmaceutically acceptable salt thereof.

* * * * *

SEQUENCE LISTING

```
Sequence total quantity: 4
SEQ ID NO: 1            moltype = DNA  length = 22
FEATURE                 Location/Qualifiers
misc_feature            1..22
                        note = A synthetic primer
source                  1..22
                        mol_type = other DNA
                        organism = synthetic construct
SEQUENCE: 1
gacaccattt ctacagttcc ag                                              22

SEQ ID NO: 2            moltype = DNA  length = 22
FEATURE                 Location/Qualifiers
misc_feature            1..22
                        note = A synthetic primer
source                  1..22
                        mol_type = other DNA
                        organism = synthetic construct
SEQUENCE: 2
cggatagctg gtgtacttgt ag                                              22

SEQ ID NO: 3            moltype = DNA  length = 22
FEATURE                 Location/Qualifiers
misc_feature            1..22
                        note = A synthetic primer
source                  1..22
                        mol_type = other DNA
                        organism = synthetic construct
```

-continued

```
SEQUENCE: 3
acagacctgc gtgctgatcg tg                                           22

SEQ ID NO: 4            moltype = DNA  length = 21
FEATURE                 Location/Qualifiers
misc_feature            1..21
                        note = A synthetic primer
source                  1..21
                        mol_type = other DNA
                        organism = synthetic construct
SEQUENCE: 4
acgagctgac ggagttgcca c                                            21
```